(12) United States Patent
Gass et al.

(10) Patent No.: US 8,589,158 B2
(45) Date of Patent: Nov. 19, 2013

(54) APPLICATION SERVER FOR REDUCING AMBIANCE NOISE IN AN AUSCULTATION SIGNAL, AND FOR RECORDING COMMENTS WHILE AUSCULTATING A PATIENT WITH AN ELECTRONIC STETHOSCOPE

(75) Inventors: Raymond Gass, Bolsenheim (FR); Michel Le Creff, Vigny (FR)

(73) Assignee: Alcatel Lucent, Paris (FR)

( * ) Notice: Subject to any disclaimer, the term of this patent is extended or adjusted under 35 U.S.C. 154(b) by 124 days.

(21) Appl. No.: 13/003,627

(22) PCT Filed: Jul. 10, 2009

(86) PCT No.: PCT/EP2009/058808
§ 371 (c)(1),
(2), (4) Date: Jul. 27, 2011

(87) PCT Pub. No.: WO2010/004025
PCT Pub. Date: Jan. 14, 2010

(65) Prior Publication Data
US 2011/0276328 A1 Nov. 10, 2011

(30) Foreign Application Priority Data

Jul. 11, 2008 (EP) .................................... 08305395

(51) Int. Cl.
*G10L 15/26* (2006.01)
(52) U.S. Cl.
USPC ........... 704/235; 704/231; 704/251; 704/246; 704/270; 704/270.1
(58) Field of Classification Search
USPC ............. 704/7, 231, 251, 257, 233, 235, 246, 704/270, 270.1; 381/73.1
See application file for complete search history.

(56) References Cited

U.S. PATENT DOCUMENTS

| | | | |
|---|---|---|---|
| 5,025,809 A | 6/1991 | Johnson et al. | |
| 6,236,862 B1 * | 5/2001 | Erten et al. | 455/501 |
| 2003/0002685 A1 | 1/2003 | Werblud | |
| 2003/0055321 A1 | 3/2003 | Watrous et al. | |
| 2004/0037429 A1 | 2/2004 | Candioty | |
| 2004/0170285 A1 * | 9/2004 | Baekgaard et al. | 381/67 |
| 2008/0298603 A1 * | 12/2008 | Smith | 381/67 |
| 2010/0189235 A1 * | 7/2010 | Um | 379/106.02 |
| 2011/0096936 A1 * | 4/2011 | Gass | 381/67 |
| 2011/0274013 A1 * | 11/2011 | Gass | 370/261 |

OTHER PUBLICATIONS

International Search Report for PCT/EP2009/058808 dated Nov. 3, 2009.
European Search Report for EP 08305395.9 dated Jan. 7, 2009.

* cited by examiner

*Primary Examiner* — Qi Han
(74) *Attorney, Agent, or Firm* — Fay Sharpe LLP

(57) ABSTRACT

An application server for reducing ambiance noise in an auscultation signal, and for recording comments while auscultating a patient with an electronic stethoscope This application server (AS) comprises: means (SPH) for receiving samples of a raw auscultation signal representing auscultation sounds mixed with ambiance sounds, this raw auscultation signal being transmitted by a first microphone (M1) embedded in a stethoscope (ES), means (SPH) for receiving samples of an ambiance signal transmitted by a second microphone (M2) in a phone (IPP1), means (ASE) for processing the samples of the auscultation signal and the samples of the ambiance signal for generating an auscultation signal without ambiance sounds, means (LBM) for sending the auscultation signal without ambiance sounds to at least the headset of said stethoscope (ES), means (VRM) for recognizing vocal sounds in the ambiance signal, and converting these vocal sounds into text for storing comments into a database (DB).

6 Claims, 3 Drawing Sheets

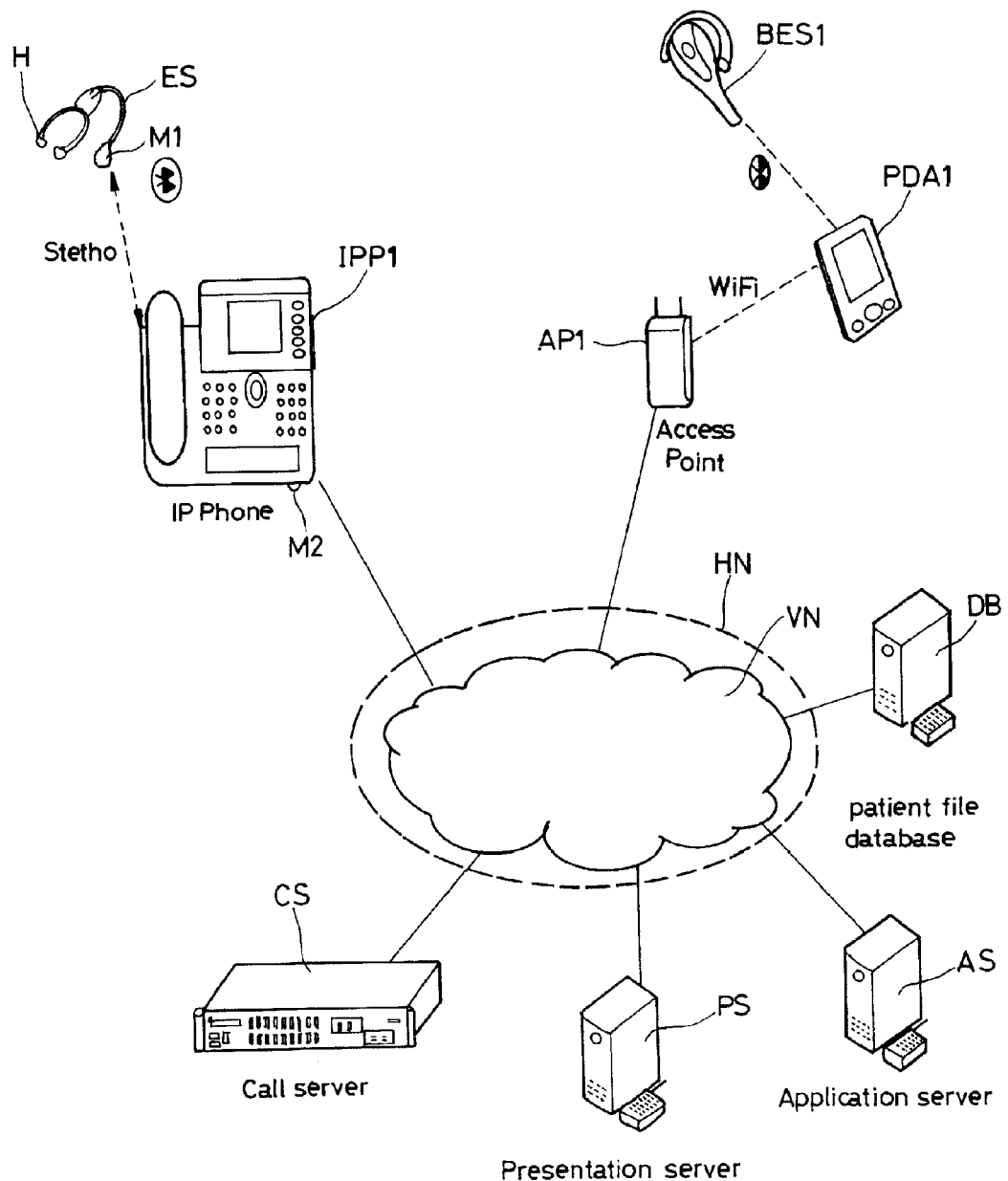
FIG_1

FIG_2
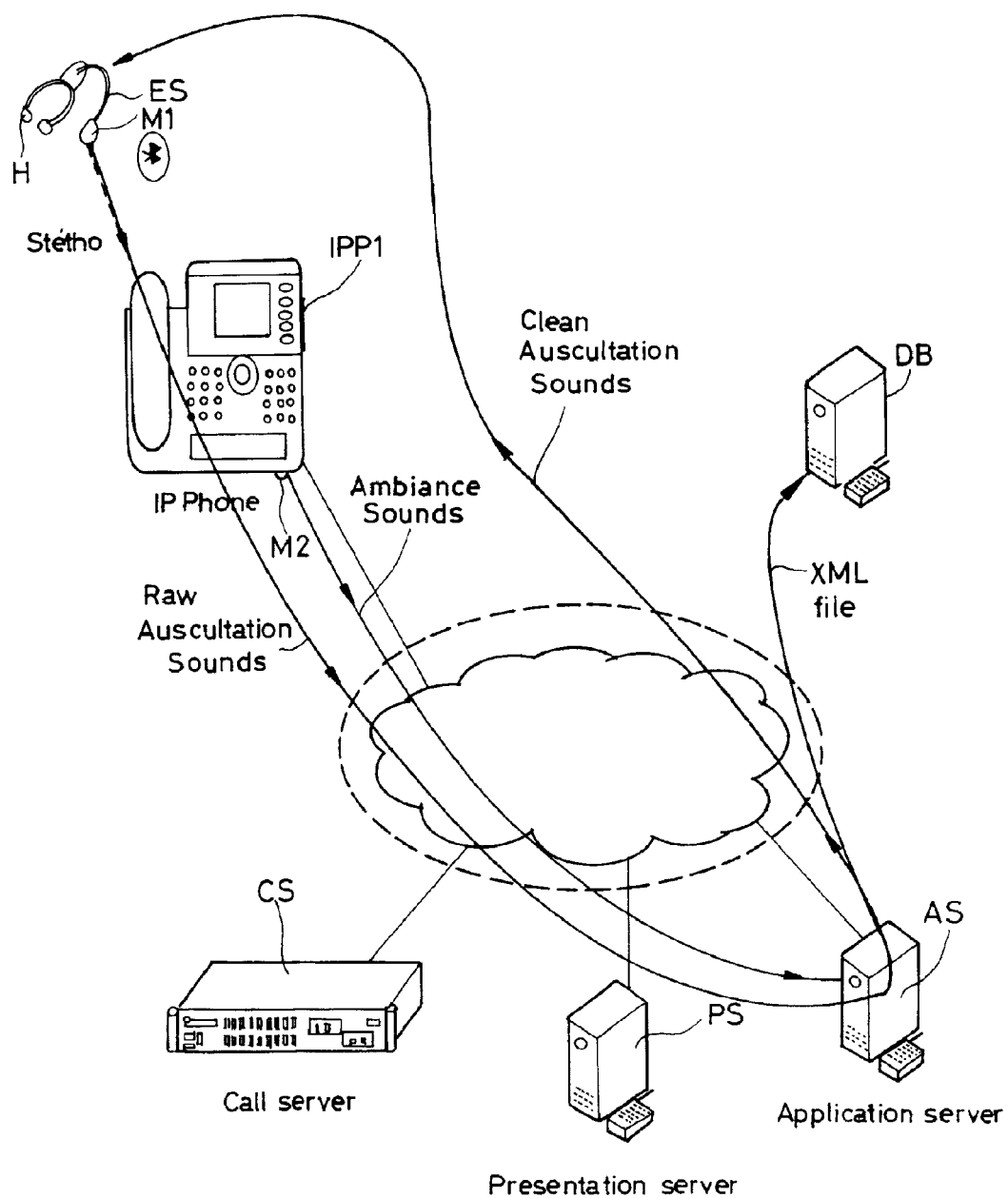

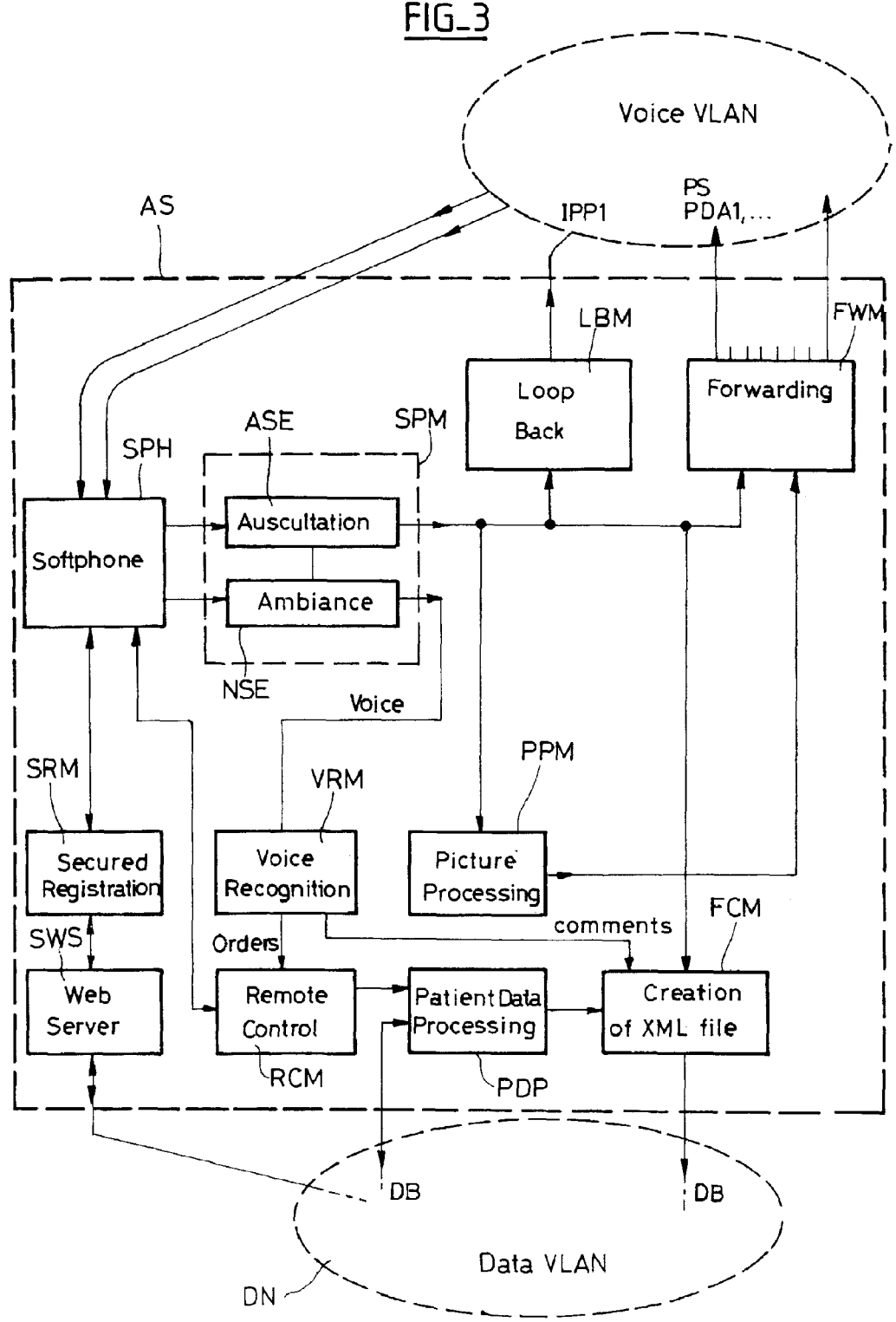

APPLICATION SERVER FOR REDUCING AMBIANCE NOISE IN AN AUSCULTATION SIGNAL, AND FOR RECORDING COMMENTS WHILE AUSCULTATING A PATIENT WITH AN ELECTRONIC STETHOSCOPE

BACKGROUND OF THE INVENTION

1. Field of the Invention

Auscultation consists in listening to sounds from an organism, in particular heart and lungs, with a stethoscope. The invention relates to an application server for reducing ambiance noise in an auscultation signal, and for recording comments while auscultating a patient with an electronic stethoscope.

2. Description of the Prior Art

There exist electronic stethoscopes of the type comprising a microphone, electronic sound processing means, and sound reproducing means, such as a loudspeaker or headphones. An electronic stethoscope gives the possibility of active amplification and filtering to any desired degree. The output of an electronic stethoscope can be linked to a personal computer or a personal digital assistant for analyzing and displaying waveforms, for instance a phonocardiogram. It can be linked to a recoding device for recording the auscultation sounds.

The major drawback with these electronic stethoscopes is that ambiance noise is also captured and amplified. The auscultation of a patient can be hampered by ambiance noise, such as cries of the patient if he/she is a baby, patient's speech, or doctor's speech. In particular, if the practitioner dictates comments for the patient's file while auscultating, the ambiance sounds are superimposed onto the auscultation sounds. Thus noise can trouble the useful sounds. It may prevent the practitioner from detecting elements that are significant on a clinical basis.

It is therefore essential to clean the auscultation sound, by canceling ambiance noise. The document US2004037429 describes an electronic stethoscope for use in an environment having a high ambiance noise level, comprising:
 a) a first microphone operative to be positioned against the person for generating a signal indicative at least one sound emanating from within the person and the ambiance noise of the environment;
 b) at least one second microphone operative to produce a signal indicative of the ambiance noise of the environment; and
 c) an ambiance noise cancellation device operatively coupled to said at least one second microphone and said headphones, said active noise cancellation system being operative to generate a signal substantially out of phase with a portion of said signal generated by said diaphragm microphone corresponding to said ambiance noise of the environment; and
 d) a headphone set operative to receive and audibly transmit said signals received from said diaphragm microphone and said ambiance noise cancellation device.

The ambiance noise cancellation device generates a signal that is approximately 180 degrees out of phase with said portion of said signal generated from said first microphone corresponding to the ambiance noise of the environment. A processor unit executes a spectral subtraction algorithm, to generate said signal being approximately 180 degrees out of phase.

The document US 2003/0002685 describes an electronic stethoscope that comprises a radio transmitter-receiver that enables to link it to a local area network comprising a server that comprises means for receiving samples of a raw auscultation signal representing auscultation sounds mixed with ambiance sounds, and sound signal processing means that can emphasize non nominal components of the auscultation signals. A processed auscultation signal is sent back to the stethoscope, up to the ears of the practitioner. It can also be recorded for medical record keeping.

A peculiar type of ambiance noise is constituted by practitioner's comments. Classically the practitioner holds a portable dictating machine in one hand and the chest piece of the stethoscope in the other hand, for recording such comments during the auscultation. These comments are later typed on a computer by a secretary, and the text file can be stored into a patient file data base.

However, it is not convenient to hold a portable dictating machine in one hand and the chest piece of a stethoscope in the other hand. In addition, dictating comments during auscultation creates an ambiance noise that is detrimental to the auscultation sounds, in particular if the auscultation signal must be recorded in the patient's medical file.

A known ambiance noise reduction device can reduce the sounds of the practitioner's comments as well as the other ambiance noises, but it does not suppress the inconvenience of holding a dictating machine in one hand, and the chest piece of the stethoscope in the other hand. A second drawback is the need of typing the dictated comments.

So, in addition to reducing the ambiance sounds in the auscultation signal, it is desirable to provide a more convenient way of recording comments into a patient file database.

This can be provided by the application server according to the invention.

SUMMARY OF THE INVENTION

The object of the invention is an application server for reducing ambiance sounds in an auscultation signal, this server being adapted to be linked to a local area network infrastructure supporting a virtual local area network supporting voice over IP telephony application, characterized in that it comprises:
for reducing ambiance sounds in an auscultation signal, and for recording comments, this server being adapted to be linked to a local area network infrastructure (HN) supporting a virtual local area network supporting voice over IP telephony application, comprising
  means for receiving samples of a raw auscultation signal representing auscultation sounds mixed with ambiance sounds;
  characterized in that it further comprises:
    means for receiving samples of an ambiance signal,
    means for processing the samples of the auscultation signal and the samples of the ambiance signal, for generating an auscultation signal without ambiance sounds,
    means for sending back the auscultation signal without ambiance sounds said virtual local area network (VN) supporting voice over IP telephony application,
    means for recognizing vocal sounds in the ambiance signal, and converting these vocal sounds into text.

According to a peculiar embodiment, the server according to the present invention further comprises:
  means for inserting this text into a file that can be stored into a database,
  and means for sending this file to a database connected to said local area network infrastructure.

This peculiar embodiment provides a convenient way of recording the practitioner's vocal comments into a patient file database, because the practitioner does not need to handle a dictating machine any more.

According to a peculiar embodiment, the server according to the present invention further comprises means for recognizing vocal orders in the text resulting from the conversion of the vocal sounds, and then controlling some functions of the application server, according to the recognized vocal orders.

This peculiar embodiment enables the practitioner to voice control the functions of a stethoscope, and the functions of a patient file data base, without degrading the auscultation signal with vocal orders because all the ambiance sounds, and in particular the vocal comments, are cancelled in the auscultation signal.

Other features and advantages of the present invention will become more apparent from the following detailed description of embodiments of the present invention, when taken in conjunction with the accompanying drawings.

BRIEF DESCRIPTION OF THE DRAWINGS

In order to illustrate in detail features and advantages of embodiments of the present invention, the following description will be with reference to the accompanying drawings. If possible, like or similar reference numerals designate the same or similar components throughout the figures thereof and description, in which:

FIG. 1 is a block diagram showing an exemplary hospital local area network supporting a voice dedicated VLAN, and comprising an embodiment of the application server according to the invention.

FIG. 2 illustrates the use of this embodiment of the application server according to the invention, for cleaning auscultation sounds, forwarding them back to the electronic stethoscope, and for extracting vocal comments, converting them to text, and storing them along with the auscultation signal, into the patient's file in a data base.

FIG. 3 schematically represents this embodiment of the application server according to the invention application server, with more details.

DETAILED DESCRIPTION OF THE PREFERRED EMBODIMENTS

FIG. 1 is a block diagram showing an exemplary hospital local area network FIN that comprises:
- A patient file database DB connected to a data dedicated VLAN (not represented on this figure).
- A voice dedicated virtual local area network (VLAN), VN, which is using the IP protocol family to route streaming packets containing voice samples, and streaming packets containing samples of physiological signals.
- A call server CS linked to the voice dedicated VLAN, VN, for establishing voice over IP communications between terminals connected to the voice VLAN VN.
- Wi-Fi access points, such as the access point AP1, linked to the voice dedicated VLAN VN. They enable users to connect Wi-Fi terminals to this network. For instance, a personal digital assistant PDA1 is connected to this access point AP1, while a Bluetooth ear set BES1 is connected to this personal digital assistant PDA1 by a Bluetooth link. The user of this equipment can place phone calls on the voice dedicated VLAN, VN, but he/she can also listen to an auscultation lesson, and look at auscultation waveforms on the display of the personal digital assistant PDA1.
- IP phones, such as the IP phone IPP1, placed at patients' bedsides. Each of these IP phones comprises a screen that can display alphanumeric characters as well as a picture. Each of these IP phones also comprises a Bluetooth interface that enables to connect an audio device bidirectionally to the voice dedicated VLAN, VN. A cordless digital stethoscope ES is connected to the IP phone IPP1 via this Bluetooth interface.
- An embodiment AS of the application server according to the invention.
- A presentation server PS.

FIG. 2 illustrates the use of the application server AS for cleaning a raw auscultation signal, representing auscultation sounds mixed with vocal comments captured by the electronic stethoscope ES, and then forwarding a cleaned auscultation sounds back to the electronic stethoscope ES, and forwarding an XML file, containing the comments in textual form and the cleaned auscultation sounds, to the database DB where they are recorded into the patient file.

The stethoscope ES comprises a headset H and a chest piece comprising a Bluetooth interface and a microphone M1. It sends samples of a raw auscultation signal representing auscultation sounds, mixed with ambiance sounds, through the voice dedicated VLAN, VN, and the IP phone IPP1. It receives samples of a cleaned auscultation signal representing auscultation sounds without ambiance sounds, through the voice dedicated VLAN, VN, and the IP phone IPP1.

The IP phone IPP1 classically comprises a microphone in the hand-set, and an additional microphone M2 integrated to the cabinet, for the hand free function. This latter is used for capturing the ambiance sounds and supplying a corresponding ambiance signal. The ambiance sounds include practitioner's vocal comments, if any.

The electronic stethoscope ES is designed so that the auscultation signal supplied by its microphone M1 can be switched to the IP phone IPP1 instead of the headset H of the stethoscope ES, and so that a clean auscultation signal supplied by the IP phone IPP1 can be switched to the headset H. So the raw auscultation signal can be sent to the application server AS, via the voice dedicated VLAN, VN, for processing, then be sent back, via the voice VLAN VN, to the ears of the user of the stethoscope ES and possibly dispatching to other terminals connected to the voice dedicated VLAN, VN.

The practitioner connects the stethoscope ES to the Bluetooth interface of the IP phone IPP1 in the classical way. Then the practitioner dials an extension number that designates the application server AS. The call is established by the call server CS in a classical way. The call set up is performed, based on that specific protocol currently used by the call server that is used inside the hospital. This specific call set up procedure becomes more and more SIP based, but proprietary protocols can also be used.

The embodiment AS of the application server according to the invention comprises means for:
- receiving the raw auscultation signal and the ambiance signal transmitted by the IP phone IPP1, respectively as two flows of data packets,
- de-encapsulating a packet containing samples of the raw auscultation signal, at the real time transport protocol level,
- de-encapsulating a corresponding packet containing samples of the ambiance signal, at the real time transport protocol level,
- processing these samples for generating separately a cleaned auscultation signal, i.e. without ambiance sounds, and an ambiance signal, this ambiance signal being mainly constituted by practitioner's vocal comments, if any, encapsulating the cleaned auscultation signal into a first packet flow addressed to the IP phone IPP1, and possibly into at least a second packet flow addressed to another terminal connected to the voice dedicated VLAN, VN, such as the personal digital assistant PDA1 represented on FIG. 1, recognizing vocal comments in the ambiance signal, converting these vocal comments into text, inserting this text into a XML file so that it can be stored into the database BD, storing this file into the patient's medical file, in the database BD.

So the application server AS cleans the raw auscultation signal by canceling the ambiance sounds, and sends the cleaned auscultation signal back to the headset H of the stethoscope ES. Simultaneously, it recognizes vocal comments, if any, among the ambiance sounds; converts them to text; and stores them into the database BD. In addition, the application server AS can process the cleaned auscultation sounds in order to enhance sound characteristics that are valuable for a diagnostic, before dispatching them to the IP phone IPP1, and possibly other terminals connected to the voice dedicated VLAN, VN.

The presentation server PS linked to the voice dedicated VLAN, VN, manages the screen and the keyboard of the IP phones of the hospital network HN for several applications that can be exploited via these IP phones. For instance, the screen and the keyboard of the IP phone IPP1 can be used for making an auscultation and for taking a phone call, at the same time. The presentation server PS generates the pictures to be displayed on the screen of the IP phone IPP1 according to the applications being currently used. In the opposite direction, the presentation server PS receives signaling messages from the IP phone IPP1, these messages corresponding to the keys that are pressed, and it forwards them to an appropriate application, in particular to the applications run on the application server AS.

For instance, if the practitioner press a key dedicated to start auscultation, the presentation server PS sends a request to the call server CS to set up a call between the IP phone IPP1 and the application server AS dealing with auscultation. When the application server AS has accepted the call, the presentation server PS then generates an updated picture to be displayed on the screen of the IP phone IPP1. This picture may comprise keywords or icons located near keys of the IP phone IPP1, and that can be dynamically assigned to peculiar functions depending of the applications currently used. When the practitioner presses a key, the presentation server PS receives a message indicating that this key has been pressed. It forwards the message to an appropriate application. If the message concerns a key dedicated to the auscultation, the message is forwarded to a remote control module of the application server AS.

A terminal connected to the voice dedicated VLAN, VN, may be an IP phone of the hospital, but it may also be any distant VOIP terminal connected via any IP supporting network, wired or wireless.

FIG. 3 is a block diagram showing more details of the exemplary embodiment AS of the application server according to the invention. The application server AS comprises a softphone SPH, i.e. a software program for making telephone calls over an IP network, using a general purpose computer. This softphone SPH enables to access the application server AS via the voice dedicated VLAN, VN. It acts like a specific telephone set connected to the voice dedicated VLAN, VN:

It will automatically accept a voice call, set up from any telephone set inside or outside the hospital network HN.

It will automatically accept a conference call, set up from any telephone set inside or outside the hospital network HN.

It will initiate a secured registration process to identify any caller.

It will terminate adequately the call set up protocol so as to be in a position to establish a voice connection over the voice dedicated VLAN, VN, without any specific requirement, neither from the calling party, nor from the call server CS.

It automatically returns to an idle state when a call is released by the terminal that has set it up.

The application server AS further comprises a sound processing module SPM, which is a software program module for:

receiving packets containing samples of the raw auscultation signal, and packets containing samples of the ambiance signal, all supplied by the softphone SPH, de-encapsulating each packet at the real time transport protocol level, processing the samples of the raw auscultation signal with an auscultation sound extraction module ASE, described below, for generating a clean auscultation signal, i.e. without ambiance sounds, processing the samples of the ambiance signal with an ambiance sound extractor NSE, for supplying an ambiance signal to the auscultation sound extraction module ASE, and for supplying a voice signal adapted to be processed for voice recognition, encapsulating the clean auscultation signal into a first packet flow addressed to the IP phone IPP1, and possibly into at least a second packet flow addressed to another terminal connected to the voice dedicated VLAN, VN, for instance the personal digital assistant PDA1, linked to Bluetooth ear set BES1.

The ambiance sound extractor NSE applies known methods for discriminating voice and noise in a signal, for extracting the vocal sounds to be processed by the voice recognition module VRM.

The auscultation sound extraction module ASE cancels the ambiance sounds that are mixed with the auscultation sounds, in the raw auscultation signal by subtracting from the raw auscultation signal a part that represents external noise or voice that have crossed the chest of the patient; assuming that there is a negligible time shift between the two signals respectively representing the ambiance sounds captured by the microphone M2 of the IP phone IPP1, and the ambiance sounds captured by the microphone M1 of the stethoscope, through the chest of the patient.

The signal processing algorithms implemented in the auscultation sound extraction module ASE mainly consider the signal distortion that is introduced by the chest.

In a preferred embodiment of the auscultation sound extraction module ASE, a low pass filtering is applied to the ambiance signal while generating the correction signal. This filtering is aimed to simulate the acoustical low pass filtering created by the chest of the patient when ambiance sounds penetrate into this chest before reaching the microphone M1 of the stethoscope.

A fixed low pass filtering and a fixed attenuation may be used for generating the correction signal for all types of patient.

However a preferred embodiment applies an adaptable low pass filtering and an adaptable attenuation, calibrated by determining the acoustical transfer function of the patient's chest. For determining this transfer function h(t), and then calculating the cleaned auscultation signal CSA(t) a method consists in:

- placing the chest piece of the stethoscope on the patient's chest, far from the heart auscultation points, in order to avoid capturing the heart sounds,
- requesting the patient to stop breathing, in order to avoid capturing the breathing sounds,
- the practitioner says a calibration sentence, for instance repeating "Stop breathing!", that is captured by both microphones, M1 providing a raw auscultation signal SA(t) containing only the ambiance sounds, i. e. the calibration phrase, and M2 providing an ambiance signal SD(t),
- calculating the acoustical transfer function H(t) of the patient's chest, by calculating the convolution product:

$$SD(t)*SA(t),$$

after this calibration phase, during the real auscultation, generating the correction signal SC(t) by calculating the convolution product:

$$SC(t)=SD(t)*H(t)$$

and then calculating the cleaned auscultation signal:

$$CSA(t)=SA(t)-SC(t)$$

The application server AS further comprises a voice recognition module VRM receiving the ambiance signal prepared by the ambiance signal extractor VSE. It converts comments and orders to text, in a classical way.

The application server AS further comprises a secured registration module SRM used to control the access to the application server AS, in particular when a practitioner is calling from a patient's room with an IP phone. This secured registration module SRM comprises a local database storing a list of the users that are allowed to access to the server AS, along with their logins and passwords. This local database is managed by classical management tools. In a specific embodiment, the local database is a MySQL database, managed through secured remote connection. The softphone SP handles the list of authorized users. It ensures control of secured connections of all the users that call it.

The application server AS further comprises a secured web server SWS, coupled to the secured registration module SRM, and that enables used to control the access to the application server AS, when a user requests access via a data dedicated VLAN, DN, supported by the hospital network HN. The access is then using the Hypertext Transfer Protocol over Secure Socket Layer (HTTPS).

The application server AS further comprises a remote control module RCM for decoding remote control commands. It supplies control signals to all the other modules of the application server AS. It collaborates with the softphone SP for receiving commands manually applied on the keyboard of the IP phone IPP1, and it collaborates with the voice recognition module VRM for receiving predefined orders vocally applied via the microphone M1 of the stethoscope ES. So, when voice paths are established over the hospital network HN, inside the voice dedicated VLAN, VN, the application server AS can receive remote control commands sent by a distant terminal for performing several operations that are needed for making an auscultation, recording an auscultation, and/or teaching an auscultation lesson. For instance: selecting a parameter for filtering the auscultation sounds, starting/stopping the recording of the auscultation signal, etc. . . .

The application server AS further comprises a loop back module LBM to loop back, at the level of the RTP (Real-time Transport Protocol), the auscultation signal, without the ambiance signal, to the terminal to which the stethoscope is connected. This loop back module LBM de-encapsulates a data packet, at the level of RTP, and permutes the source address and the destination address. For instance, the loop back module LBM loops back an incoming RTP channel so as to send the auscultation sounds, without vocal sounds, back to the headset of this stethoscope ES, via the IP phone IPP1 at the patient's bedside. This enables a practitioner to listen to cleaned auscultation sounds in a quasi real-time operation (Quasi real-time meaning the roundtrip delay over the voice dedicated VLAN, VN, between the IP phone inside the patient's room and the softphone SPH of the application server AS. Ideally, the roundtrip delay should be maintained low enough to avoid disturbance to a practitioner).

The application server AS further comprises a picture processing module PPM receiving the cleaned auscultation from the auscultation sound extraction module SPM, for periodically elaborating pictures (a cardiophonogram) that will be sent over UDP (User Datagram Protocol), via the presentation server PS, to be displayed on the screen of a terminal that cannot elaborate such pictures, for instance the IP phone IPP1 at the patient's bedside. The picture processing module PPM of the application server AS processes the cleaned auscultation signal for continuously generating a sliding waveform in real time. A method for such processing is described in the document U.S. Pat. No. 5,025,809 incorporated here by reference. However the IP phone IPP1 has not enough resources to continuously calculate and display the streaming video corresponding to such a waveform. The picture processing module PPM elaborates a curve that is the visual representation of the analogue signal corresponding to the auscultation sounds, and then takes periodic pictures of the curve. It forwards the series of pictures to the presentation server PS for displaying these pictures on a screen of the IP phone IPP1.

The logical distinction between the application server AS and the presentation server PS is a functional split only. Both applications may run on the same machine.

The presentation server PS continuously receives pictures of the curve generated by the application server AS in real time. Theses pictures are transported from the application server AS to the presentation server PS via a VLAN supporting data (not represented on the FIG. 3) supported by the hospital local area network HN.

The presentation server PS refreshes the picture displayed on the screen of the IP phone IPP1, via the voice dedicated VLAN, VN, with a rate that is appropriate for the performance of the IP phone IPP1. As an example, a refresh rate of one picture per second, is adequate to provide a good compromise between processing load, network load, and visual comfort during auscultation. The files representing these pictures are compressed. The picture rate and the compression rate are compatible with the limited bandwidth of the connection to the IP phones, and with the limited bandwidth of the displaying means of the IP phones, in order that the pictures can be displayed in real time. Each picture is a kind of photograph of the auscultation signal, compressed with the classical JPEG format as an example, by the picture processing module PPM of the presentation server AS.

In the opposite direction, the presentation server PS receives signaling messages from the IP phone IPP1, these messages corresponding to the keys that are pressed, and it forwards them to an appropriate application, in particular to the applications run on the application server AS.

For instance, if the practitioner press a key dedicated to start auscultation, the presentation server PS sends a request to the call server CS to set up a call between the IP phone IPP1 and the application server AS dealing with auscultation. When the application server AS has accepted the call, the presentation server PS then generates an updated picture to be displayed on the screen of the IP phone IPP1. This picture may comprise keywords or icons located near keys of the IP phone IPP1, and that can be dynamically assigned to peculiar functions depending of the applications currently used. When the practitioner presses a key, the presentation server PS receives a message indicating that this key has been pressed. It forwards the message to an appropriate application. If the message concerns a key dedicated to the auscultation, the message is forwarded to the remote control module RCM of the application server AS.

The application server AS further comprises a forwarding module FWM that can makes n unicasts of an incoming RTP flow directly to n outgoing RTP flows towards n terminals connected to the voice dedicated VLAN, for instance for teaching auscultation to n students simultaneously. The forwarding module FWM can forward the auscultation sounds, without the vocal sounds, supplied by the sound processing module SPM. It can also forward a series of pictures, supplied by the picture processing module PPM, to a terminal that cannot elaborate such pictures, for instance the IP phone IPP1 at the patient's bedside, via the presentation server PS.

The application server AS further comprises a module PDP for processing patient data. It can consult the patient file database DB to retrieve some administrative data about a patient. It can also control the writing of new data into the database DB. It receives, from the voice recognition module VRM, some text resulting from the conversion of vocal sounds into text. The voice recognition module VRM has eliminated, from this text, groups of words that are vocal orders, and it has constituted a text file composed of the practitioner's comments (For instance, the location where the sounds have been collected) and of administrative data.

The application server AS further comprises a module FCM for the creation of an XML file wherein a series of samples of the cleaned auscultation signal, supplied by the auscultation sound extraction module SPM, are placed together with the text file prepared by the patient data processing module PDP. Then this XML file is sent over the data dedicated VLAN, DN, to be stored into the patient database DB.

The softphone SPH which is running inside the application server AS behaves like a normal phone, regardless of the evolution of a call (transfer, second call, call transfer, call park, call pick up, etc): When a terminal calls the application server AS, the call server CS invites the softphone SPH to a call. The softphone SPH accepts the call. When the call has been set up, the sound processing module SPM, in the application server AS, cancels the ambiance sounds in the raw auscultation signal. Then the loop back module LBM of the application server AS sends the cleaned auscultation signal back to the calling terminal. In the present case, the cleaned auscultation signal is sent back to the IP phone IPP1, and up to the headset H of the stethoscope ES, via the Bluetooth link.

The voice recognition module VRM enables the practitioner to use vocal order for some orders, for instance starting/stopping the recording of the cleaned auscultation sounds and comments (in parallel but into separate data files) into the database DB. This is far easier than pressing keys while holding the stethoscope on the patient's chest.

The practitioner is in communication with the application server AS via the presentation server PS, as explained above. The secured registration module SRM of the application server AS received the extension number of the IP phone IPP1 when the practitioner was calling. It also received the practitioner's name when he/she logged in.

The practitioner presses some keys of the IP phone IPP1 to command the application server AS to start the recording of the cleaned auscultation signal in the auscultation sound extractor ASE of the sound processing module SPM. The presentation server PS forwards, to the application server AS, the signaling messages indicating what keys have been pressed.

Later, the practitioner presses some keys of the IP phone IPP1 to command the application server AS to stop the recording of the cleaned auscultation signal in the auscultation sound extractor ASE. Then the practitioner presses some keys of the IP phone IPP1 to document the auscultation sound recorded in the auscultation sound extractor ASE of the sound processing module SPM. In particular, he/she indicates the auscultation zone by pressing keys or moving a navigation button, on the IP phone IPP1.

Then the practitioner presses some keys to command the application server AS to store the sound record and annexed textual information into the patient file database DB.

The file creation module FCM makes an XML file containing:

The auscultation sound record, in .wav file.
The extension number of the IP phone IPP1, which will enable to retrieve the room number and the patient's name.
The practitioner's name.
The auscultation zone.
Textual comments.

Then the application server AS sends this XML file to the database DB, via a data dedicated local area network supported by the hospital network HN.

This information can be retrieved later via the web server of the patient file database DB and the application server AS. A user who has an appropriate access right for consulting a patient file and who has an IP terminal connected to the voice dedicated VLAN, VN, calls the softphone SPH of the application server AS. The user accesses to the patient file database DB via the secured registration module SRM of the application server AS. An XML file is read in the data base DB and then is sent to the patient data processing module PDP. This latter opens the XML file, then extracts the auscultation sounds and sends them to the terminal of the requesting user, via the voice dedicated VLAN, VN. It also extracts the textual comments but it does not send them directly to the terminal. It sends them to the presentation PS in order to adapt their format to the display capacity of the destination terminal. Then the presentation PS sends the textual data to the terminal via the voice dedicated VLAN, VN.

This auscultation signal can also be retrieved to be listened to during an auscultation lesson.

There is claimed:

1. An application server for reducing ambiance sounds in an auscultation signal, and for recording comments, the server being adapted to be linked to a local area network infrastructure supporting a virtual local area network supporting voice over IP telephony application, comprising:
a softphone configured to receive samples of a raw auscultation signal representing auscultation sounds mixed with ambiance sounds and receive samples of an ambiance signal;

an auscultation sound extraction module configured to process the samples of the auscultation signal and the samples of the ambiance signal, for generating an auscultation signal without ambiance sounds;
a loop back module configured to send back the auscultation signal without ambiance sounds via said virtual local area network supporting voice over IP telephony application; and
a voice recognition module configured to recognize vocal sounds in the ambiance signal, and converting these vocal sounds into text.

2. An application server according to claim 1, characterized in that it further comprises:
a patient data processor configured to insert the text into a file that can be stored into a database, and
a remote control module configured to send the file via the local area network infrastructure.

3. An application server according to claim 1, wherein the voice recognition module is configured to recognize vocal orders in the text resulting from the conversion of the vocal sounds, and then control some functions of the application server, according to the recognized vocal orders.

4. An application server according to claim 1, wherein the auscultation sound extraction module is configured to processing the samples of the raw auscultation signal and the samples of the ambiance signal to generate an auscultation signal without ambiance sounds, and add to the raw auscultation signal a correction signal that is a function of the ambiance signal.

5. An application server according to claim 4, wherein the auscultation sound extraction module adding to the raw auscultation signal a correction signal that is a function of the ambiance signal, is configured to:
calculate the acoustical transfer function H(t) of the chest of the patient, by calculating the convolution product SD(t)*SA(t), where SD(t) is the ambiance signal and SA(t) is the raw auscultation signal during a calibration phase;
generate a correction signal SC(t) by calculating the convolution product SC(t)=SD(t)*H(t), after the calibration phase, during a real auscultation; and
calculate the cleaned auscultation signal CSA(t)=SA(t)−SC(t), after the correction signal is calculated.

6. An application server according to claim 1, wherein the loop back module, for sending the auscultation signal without ambiance sounds at least to the headset of the stethoscope, is further configured to:
de-incapsulate packets received from the stethoscope at the real time transport protocol level, and extract the source address of each packet, using the extracted address, while encapsulating the auscultation signal without voice sound into packets at the real time transport protocol level, to constitute a destination address in order to forward the packet back to the terminal to which the stethoscope is connected.

\* \* \* \* \*

UNITED STATES PATENT AND TRADEMARK OFFICE
CERTIFICATE OF CORRECTION

| | | |
|---|---|---|
| PATENT NO. | : 8,589,158 B2 | Page 1 of 1 |
| APPLICATION NO. | : 13/003627 | |
| DATED | : November 19, 2013 | |
| INVENTOR(S) | : Gass et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 236 days.

Signed and Sealed this
Twenty-fifth Day of August, 2015

Michelle K. Lee
*Director of the United States Patent and Trademark Office*